United States Patent [19]

Daum et al.

[11] Patent Number: 5,734,076
[45] Date of Patent: Mar. 31, 1998

[54] 4,4'-METHYLENE-BIS-(3-CHLORO-2,6-DIALKYLPHENYLISOCYANATES)

[75] Inventors: Ulrich Daum, Hofstetten; Peter Hardt, Visp, both of Switzerland

[73] Assignee: Lonza AG, Gampel/Valais, Switzerland

[21] Appl. No.: 776,714

[22] PCT Filed: Aug. 16, 1995

[86] PCT No.: PCT/EP95/03260

§ 371 Date: Mar. 20, 1997

§ 102(e) Date: Mar. 20, 1997

[87] PCT Pub. No.: WO96/05171

PCT Pub. Date: Feb. 22, 1996

[30] Foreign Application Priority Data

Aug. 17, 1994 [CH] Switzerland ............... 2535/94

[51] Int. Cl.⁶ ............................................. C07C 249/00
[52] U.S. Cl. ................. 560/359; 560/347; 528/44; 528/68
[58] Field of Search ............................ 560/347, 359; 528/44, 68

[56] References Cited

U.S. PATENT DOCUMENTS 3,426,025  2/1969  Smeltz et al. .
5,028,685  7/1991  Ho et al. .

FOREIGN PATENT DOCUMENTS 0220641  5/1987  European Pat. Off. .
852651  10/1960  United Kingdom .

OTHER PUBLICATIONS

Ullmanns Encykl. D. techn. Chemie, 4th Ed., vol. 13, pp. 351 ff. 1977.

Saechtling, Kunststoff Taschenbuch, 24th Ed., published in Carl Hauser Verlag, Munich, (1989), pp. 429 ff.

*Primary Examiner*—Samuel Barts
*Attorney, Agent, or Firm*—Fisher, Christen & Sabol

[57] ABSTRACT

The 4,4'-methylene-bis-(3-chloro-2,6-dialkylphenylisocyanates) of the general formula

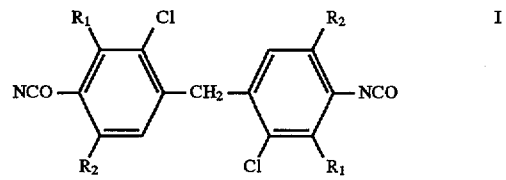

are new polyisocyanates for the production of PU systems with high chemical stability and good thermal stability.

10 Claims, No Drawings

4,4'-METHYLENE-BIS-(3-CHLORO-2,6-DIALKYLPHENYLISOCYANATES)

This application is a 371 of PCT/EP95/03260 filed Aug. 16, 1995.

BACKGROUND OF THE INVENTION

1. Field of the Invention

The invention relates to 4,4'-methylene-bis-(3-chloro-2,6-dialkylphenylisocyanates) of the general formula:

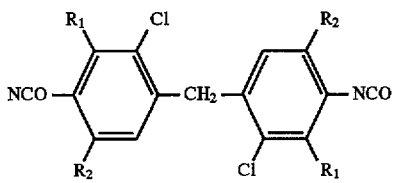

in which $R_1$ means an alkyl group with 1 to 6 C atoms and $R_2$ means chlorine or an alkyl group with 1 to 6 C atoms, a process for preparing the said polyisocyanates, and the use of the said polyisocyanates in polyurethane (PU) systems.

PU systems are defined below as polyurethane systems that contain urethane groups and/or urea groups.

BACKGROUND ART

Toluene-2,4-diisocyanate and/or toluene-2,6-diisocyanate, abbreviated TDI, or diphenylmethane-4,4'-diisocyanate, abbreviated MDI, continue to be of considerable importance as polyisocyanate components in the production of PU systems.

A major drawback of TDI is its high toxicity. Although the compound is handled on an industrial scale with the most stringent safety precautions possible, it carries a considerable risk potential.

A complete switch to the less toxic MDI is also only conditionally possible since MDI, owing to its high reactivity, can be processed with polyols, but not with aromatic polyamines.

In addition, the PU systems that are based on TDI and MDI are limited, in terms of their temperatures of use, to a maximum of 100° C.

BROAD DESCRIPTION OF THE INVENTION

The object of this invention was consequently to develop polyisocyanates that are not highly toxic, have lower reactivity than MDI, and can be processed with the conventional and new PU processing process. The goal of developing chemically stable PU systems that can be used at temperatures of above 100° C. was associated with the object.

These objects are achieved with the polyisocyanates of the above-mentioned general formula I according to the invention.

$R_1$ and $R_2$ mean a $C_1$–$C_6$-alkyl group which can be the same in meaning or different and may suitably stand for methyl, ethyl, n- or i-propyl, n-, i- or t-butyl, pentyl and its isomers and hexyl and its isomers. $R_1$ and $R_2$ are preferably the same in meaning and stand for one of the above-mentioned $C_1$–$C_4$-alkyl groups.

The preferred polyisocyanate is the 4,4'-methylene-bis-(3-chloro-2,6-diethylphenylisocyanate) with the meaning of $R_1$ and $R_2$ are each ethyl.

The production of the polyisocyanates according to the invention is carried out in the known way by reacting the corresponding polyamine with phosgene or a phosgene-releasing compound, such as, di- or triphosgene (cf., e.g., Ullmanns Encykl. d. techn. Chemie [Ullmann's Encyclopedia of Industrial Chemistry], 4$^{th}$ Edition, Volume 13, pp. 351 ff).

The corresponding polyamines are described in European Application A 0 220 641. 4,4'-Methylene-bis-(3-chloro-2,6-diethylaniline) (M-CDEA) is the preferred polyamine.

The phosgenation is carried out suitably in the presence of an inert solvent such as, toluene or chlorobenzene at elevated temperature. The reaction generally proceeds virtually quantitatively.

The resulting polyisocyanates have a high purity.

The processing of the polyisocyanates according to the invention into PU systems is carried out basically in a known way by reaction with compounds with at least two hydrogen atoms that are active compared to polyisocyanates and optionally chain-lengthening agents and optionally in the presence of commonly used catalysts and optionally other additives (cf. Saechtling, Kunststoff Taschenbuch [Plastics Notebook], 24$^{th}$ Edition, published in Carl Hauser Verlag, Munich 1989, pp. 429 if).

It is also possible to use mixtures of the polyisocyanates according to the invention with other aliphatic or aromatic polyisocyanates or prepolymers of polyisocyanates or prepolymers that are based on mixtures of polyisocyanates with aliphatic or aromatic polyisocyanates.

Suitable representatives of compounds with at least two hydrogen atoms that are active compared to polyisocyanates are especially polyols, such as, e.g., polyether polyols, polyester polyols, or other polyols, (e.g., polycaprolactones). Suitable representatives of chain-lengthening agents are polyamines, such as, e.g., the aromatic diamines MOCA, M-CDEA, mixtures of M-CDEA with aromatic or aliphatic diamines or polyols or isomer mixtures of dimethylthiotoluenediamine (ibid., p. 430, or European Published Patent Application No. A 220,641).

In addition, all commonly used catalysts, such as, tetramethylbutanediamine (TMBDA), diazabicyloocatane (DABCO), dibutyltin dilaurate (DBTC) or organic heavy metal compounds, can be used individually or in combination with additives, such as, softeners, stabilizers, fireproofing agents, propellants, or fillers (ibid. p. 430).

A great advantage of the polyisocyanates according to the invention lies in that fact that they can be processed in the standard PU processing processes, such as, the one-shot RIM process, the two-shot prepolymer process, or the two-shot direct process.

In accordance with the preferred use of polyisocyanates in the PU-elastomer sector or especially in the PU-casting elastomer sector, preference is given to the prepolymer process.

The polyisocyanates according to the invention are suitably used in a polyurethane system that can be produced by reacting a a)   4,4'-methylene-bis-(3-chloro-2,6-dialkylphenylisocyanate) of general formula I with b) compounds with at least two hydrogen atoms that are active compared to isocyanates and optionally c) chain-lengthening agents optionally in the presence of commonly used catalysts and optionally other additives.

Preferred is a polyurethane system that can be produced by reacting a a)   4,4'-methylene-bis-(3-chloro-2,6-dialkylphenylisocyanate) of general formula I with b) compounds with at least two hydrogen atoms that are active compared to isocyanates, preferably as described above, and c) an aromatic diamine as a chain lengthener in the presence of the above-mentioned commonly used additives.

Especially preferably, a 4,4'-methylene-bis-(3-chloro-2,6-dialkylaniline), especially the 4,4'-methylene-bis-(3-chloro-2,6-diethylaniline), is used as an aromatic diamine either individually or as a component of a mixture with other aromatic or aliphatic diamines or with polyols, and 4,4'-methylene-bis-(3-chloro-2,6-diethylphenyl-isocyanate) is used as component a).

The PU systems that are produced on the basis of new polyisocyanates according to the invention are distinguished by high chemical stability that is unexpected in comparison to known PU systems and by a temperature of use of up to 180° C..

These PU systems according to the invention are therefore used mainly in the PU-elastomer sector—especially in the casting-elastomer sector—for the production of, e.g., rollers, wheels, roller coatings, insulators, seals, or sealing compounds. It is eminently possible, however, to use the PU systems for spray-coating or for PU foams.

DETAILED DESCRIPTION OF THE INVENTION

EXAMPLE 1a

Production of 4,4'-methylene-bis-(3-chloro-2,6-diethylphenylisocyanate)

100 g (0.26 mmol) of 4,4'-methylene-bis-(3-chloro-2,6-diethylaniline) was introduced into 1000 g of dichlorobenzene in an autoclave at room temperature. 57 g (0.58 mol) of phosgene was introduced into this solution over a period of 30 minutes. The reaction mixture was stirred in a sealed autoclave at 80° C. for 1 hour. Then, it was depressurized, and the hydrochloric acid that was produced, the excess phosgene, and the solvent were removed. In this case, the title product resulted in a yield of 110 g (98% of theory). Other data concerning the product is:

IR (KBr): 2288.1 cm$^{-1}$ $^1$H-NMR (CDCl$_3$, 400 MHz) in ppm: 6.69 s, 2H; 4.12 s, 2H; 2.91 q, 4H, J=7.5 Hz; 2.59 q, 4H, J=7.6 Hz; 1.20 t, 6H, J=7.6 Hz; 1.15 t, 6H, J=7.5 Hz.

EXAMPLE 1b

Analogously to Example 1a, but with the solvent toluene, the title product was obtained in a yield of 109 g.

Examination of 4,4'-Methylene-bis-(3-chloro-2,6-diethylphenylisocyanate) in Comparison with Isocyanates from the Prior Art in PU Systems 1. Isocyanates Used MCDE-I 4,4'-Methylene-bis-(3-chloro-2,6-diethylphenylisocyanate)=compound according to the invention MDE-I 4,4'-methylene-bis-(2,6-diethylphenylisocyanate) =comparison substance MDI 4,4'-methylene-bis-phenylisocyanate=comparison substance 2. Production of Prepolymers (Component A)

Prepolymer 1 (Invention)

Prepolymer based on polytetramethylene ether glycol (PTMG; Tetraethane 650, Du Pont), with a molecular weight of 650 and MCDE-I 1850 g=4 mol of 94% MCDE-I was melted under nitrogen (N$_2$) at 80° C., introduced into a reaction flask, and intimately mixed with 1300 g of PTMG=2 mol over 30 minutes while being stirred. The PTMG is linear and was dehydrated before addition to isocyanate for 1 hour at 100° C. and under a vacuum of 2500 Pa. After the addition of PTMG was completed, it was then stirred for 2 more hours at 90° C. under N$_2$.

A prepolymer with a content of 5.2% of free NCO groups was obtained. This prepolymer is referred to as "PTMG 650-MCDE-I."

Prepolymer 2 (Invention)

Prepolymer based on polytetramethylene ether glycol (PTMG; Terathane 2000, Du Pont) with a molecular weight of 2000 and MCDE-I 1234 g=2.67 mol of 95% MCDE-I was melted under N$_2$ at 80° C., introduced into a reaction flask, and intimately mixed with 2133 g=1.066 of PTMG over 30 minutes while being stirred. The PTMG is linear and was dehydrated before addition to isocyanate for 1 hour at 100° C. and under a vacuum of 2500 Pa. After the addition of PTMG was completed, it was then stirred for 2 more hours at 90° C. under N$_2$.

A prepolymer with a content of 3.96% of free NCO groups was obtained. This prepolymer is referred to as "PTMG 2000-MCDE-I."

Prepolymer 3 (Invention)

Prepolymer based on polycaprolactone glycol (PCL; CAPA 220, Interox) with a molecular weight of 2000 and MCDE-I 1245 g=2.7 mol of 94% MCDE-I was melted under N$_2$ at 80° C., introduced into a reaction flask, and intimately mixed with 2133 g=1.066 mol of PCL over 30 minutes while being stirred. The PCL is linear and was dehydrated before addition to isocyanate for I hour at 100° C. and under a vacuum of 2500 Pa. After the addition of PCL was completed, it was then stirred for 2 more hours at 90° C. under N$_2$.

A prepolymer with a content of 3.92% of free NCO groups was obtained. The prepolymer is referred to as "PCL 2000-MCDE-I."

Prepolymer 4 (Comparison)

Prepolymer based on PTMG (Terathane 2000, Du Pont) with a molecular weight of 2000 and MDE-I 1158 g=3 mol of 94% MDE-I was melted under N$_2$ at 80° C., introduced into a reaction flask, and intimately mixed with 2400 g=1.2 mol of PTMG over 30 minutes while being stirred. The PTMG is linear and was dehydrated before addition to isocyanate for 1 hour at 100° C. and under a vacuum of 2500 Pa. After the addition of PTMG was completed, it was then stirred for 2 more hours at 90° C. under N$_2$.

A prepolymer with a content of 4.32% of free NCO groups was obtained. We refer to this prepolymer as "PTMG 2000-MDE-I."

Prepolymer 5 (Comparison)

Prepolymer based on PCL (CAPA 220, Interox) with a molecular weight of 2000 and MDE-I If the PTMG in prepolymer 4 is replaced by the same amount of PCL, a prepolymer with a content of 4.23% of free NCO groups is obtained under otherwise identical conditions. This prepolymer is referred to as "PCL 2000-MDE-I."

Prepolymer 6

Prepolymer based on PCL (CAPA 220, Interox) with a molecular weight of 2000 and MDI.

400 g=1.6 mol of MDI was melted under $N_2$ at 60° C., introduced into a reaction flask, heated to 80° C. and intimately mixed with 1000 g=0.5 mol of PCL over a period of 10 minutes while being stirred. The PCL is linear and was dehydrated before addition to isocyanate for 1 hour at 100° C. and under a vacuum of 2500 Pa. After the addition of PCL was completed, it was then stirred for 2 more hours at 80° C. under $N_2$.

A prepolymer with a content of 6.6% of free NCO groups was obtained. This polymer is referred to as "PCL 2000-MDI."

3. Component B

Component B is either the melted diamine* or the clear degassed solution, cooled to processing temperature (80° C.), of the diamine or diamine mixture in question in the corresponding polyol. In addition, the solutions in the polyol contain an organic bismuth compound (Coscat® 83 catalyst from the CasChem. Inc., New Jersey) relative to the overall system (components A+B).

* I 4,4'-Methylene-bis-(3-chloro-2,6-diethylaniline) M-CDEA; II diamine mixture, Luvocure MUT-HT, Lehmann & Voss; III mixture of 2,4 and 2,6 isomers of dimethylthiotoluenediamine, Ethacure 300, Albemarle Inc.

4. Preparation of the Test Piece

The prepolymer (component A) and the diamines (chain lengtheners; component B) were intimately mixed at a molar ratio of 1:0.95, i.e., NCO groups to the sum of free OH and $NH_2$ groups, at 80° C. for 30 seconds, poured into a metal mold, preheated to 110° C., with inside dimensions of 200*200*2 (in mm), and finally pressed at the start of gelling (pot life) in a press at 200 bar and 110° C.. After setting was completed (demolding time), it was demolded and subsequently tempered at 110° C. for 16 hours. Test pieces were punched out of the hardened elastomers.

5. Test Parameters

| | |
|---|---|
| Hardness Shore A and Shore D | DIN 53505 |
| Tear resistance [N/mm] | DIN 53515 |
| Tensile strength [N/mm²] | DIN 53504 |
| Tension at 100% elongation | DIN 53504 |
| Elongation at break % | DIN 53504 |

TABLE I

RESULTS WITH DIAMINE M-CDEA (I)

| Prepolymer No. | "I" in Comp. B in Mol % | "Proportion by weight" of comp. B per 100 comp. | Pot Life | Demolding Time | Hardness/Room Temperature Shore A | Hardness/Room Temperature Shore D | Hardness/ 175° C. Shore A | Tear Resistance [N/mm] | Tensile Strength [N/mm²] | Stress at 100% Elongation [N/mm²] | Elongation at Break % |
|---|---|---|---|---|---|---|---|---|---|---|---|
| 1 (Invention) | 100 | 21.0 | 2'00" | 20' | 99 | 69 | 99 | — | — | — | — |
| 2 (Invention) | 100 | 100 | 2'30" | 20' | 98 | 45 | | 53.3 | 19.7 | 9.2 | 433 |
| 2 (Invention) | 66 | 40.0 | 2'00" | 45' | 91 | 33 | | 47.7 | 18.3 | 5.2 | 809 |
| 4 (Compar.) | 100 | 18.2 | 3'00" | 45' | 97 | 43 | | 47.7 | 8.6 | 7.5 | 388 |
| 4 (Compar.) | 66 | 44.0 | 7'30" | 60' | 91 | 28 | | 35.0 | 15.0 | 4.5 | 854 |
| 3 (Invention) | 100 | 16.0 | 2'30" | 20' | 98 | 52 | 97 | 73.5 | 17.7 | 11.4 | 353 |
| 3 (Invention) | 66 | 38.0 | 2'30" | 45' | 92 | 37 | | 59.4 | 25.7 | 5.7 | 593 |
| 5 (Compar.) | 100 | 18.7 | 5'00" | 60' | 98 | 45 | 95 | 64.2 | 12.1 | 9.2 | 440 |
| 5 (Compar.) | 66 | 45.0 | 5'10" | 60' | 92 | 32 | — | 50.2 | 22.8 | 5.1 | 750 |
| 6 (Compar.) | 66 | 72.0 | 19" | 9' | 88 | — | — | 64.0 | 35.1 | — | — |
| 6 (Compar.) | 100 | 30.0 | 20" | 5' | 98 | 55 | — | 74.0 | 25.6 | — | — |

TABLE 2

Results with the Diamino Mixture Luvocure MUT-HT from Lehmann & Voss (II)

| Prepolymer No. | Weight ratio of prepolymer: comp. B | Pot Life | Demolding Time | Hardness/Room Temperature Shore A | Hardness/Room Temperature Shore D | Hardness/ 175° C. Shore A | Tear propagation Resistance [N/mm] | Tensile Strength [N/mm²] | Stress at 100% Elongation [N/mm²] | Elongation at Break % |
|---|---|---|---|---|---|---|---|---|---|---|
| 2 (Invention) | 100:20.5 | 2'00" | 40' | 97 | 46 | 95 | 60.9 | 17.2 | 9.1 | 510 |
| 4 (Compar.) | 100:22.0 | 4'30" | 45' | 97 | 40 | 93 | 50.2 | 13.9 | 7.0 | 754 |
| 3 (Invention) | 100:19.0 | 2'40" | 40' | 98 | 47 | 95 | 76.8 | 20.7 | 9.7 | 464 |
| 5 (Compar.) | 100:22.5 | 5'20" | 60' | 97 | 46 | 95 | 60.9 | 17.2 | 9.1 | 510 |

TABLE 3

Results with the Diamine-Isomer Mixture Ethacure 300 (2.4 and 2.6 Isomers of Dimethylthiotoluenediamine) from Albemarle Inc. USA

| Prepolymer No. | Weight ratio of prepolymer: comp. B | Pot Life | Demold-ing Time | Hardness/Room Temperature Shore A | Hardness/Room Temperature Shore D | Hardness/ 175° C. Shore A | Tear propagation Resistance [N/mm] | Tensile Strength [N/mm²] | Stress at 100% Elongation [N/mm²] | Elongation at Break % |
|---|---|---|---|---|---|---|---|---|---|---|
| 1 (Invention) | 100:12.0 | 1'30" | 13' | 99 | 67 | 95 | 100.5 | 32.0 | 26.1 | 165 |
| 2 (Invention) | 100:9.6 | 3'30" | 20' | 95 | 41 | | 48.8 | 35.4 | 7.4 | 525 |
| 4 (Compar.) | 100:10.2 | 6'20" | 45' | 93 | 33 | | 31.6 | 13.1 | 5.9 | 658 |
| 3 (Invention) | 100:9.0 | 4'00" | 20' | 95 | 40 | | 66.6 | 42.4 | 8.2 | 479 |
| 5 (Compar.) | 100:10.5 | 6'20" | 60' | 94 | 36 | | 45.0 | 18.1 | 6.9 | 571 |

What is claimed is:

1. A 4,4'-Methylene-bis-(3-chloro-2,6-dialkylphenylisocyanates) of the formula:

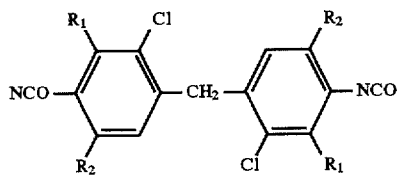

wherein $R_1$ means an alkyl group having 1 to 6 C atoms and $R_2$ means chlorine or an alkyl group having 1 to 6 C atoms.

2. 4,4'-Methylene-bis-(3-chloro-2,6-diethylphenylisocyanate).

3. A process for the production of a 4,4'-methylene-bis-(3-chloro-2,6-dialkylphenylisocyanate) of the formula:

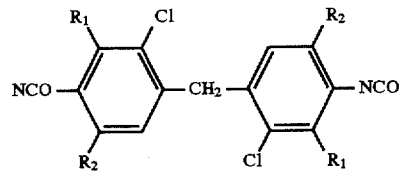

wherein $R_1$ means an alkyl group having 1 to 6 C atoms and $R_2$ means chlorine or an alkyl group having 1 to 6 C atoms, comprising reacting 4,4'-methylene-bis-(3-chloro-2,6-dialkylaniline) of the formula:

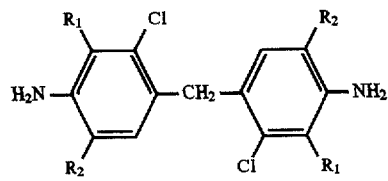

wherein $R_1$ and $R_2$ have the above-mentioned meanings, with phosgene or a phosgene-releasing compound.

4. A process comprising using a 4,4'-methylene-bis-(3-chloro-2,6-dialkylphenylisocyanate) of the formula:

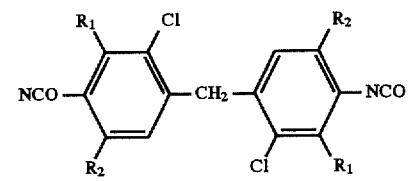

wherein $R_1$ means an alkyl group having 1 to 6 C atoms and $R_2$ means chlorine or an alkyl group having 1 to 6 C atoms, for the production of a polyurethane system.

5. The process according to claim 4 wherein the compound of formula I is 4,4'-methylene-bis-(3-chloro-2,6-diethylphenylisocyanate).

6. A polyurethane system that has been produced by reacting:
   (a) a 4,4'-methylene-bis-(3-chloro-2,6-dialkylphenylisocyanate) of the formula:

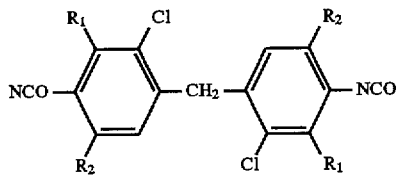

wherein $R_1$ means an alkyl group having 1 to 6 C atoms and $R_2$ means chlorine or an alkyl group having 1 to 6 C atoms, with
   (b) compounds with at least two hydrogen atoms that are active compared to isocyanates and, optionally,
   (c) chain-lengthening agents, optionally in the presence of commonly used catalysts and optionally other additives.

7. The polyurethane system according to claim 6 that has been produced by reacting:
   (a) a 4,4'-methylene-bis-(3-chloro-2,6-dialkylphenylisocyanate) with
   (b) a compound having at least two hydrogen atoms that are active compared to isocyanates, and
   (c) an aromatic diamine as a chain-lengthening agent, optionally in the presence of commonly used catalysts and optionally other additives.

8. The polyurethane system according to claim 7 wherein the aromatic diamine is a 4,4'-methylene-bis-(3-chloro-2,6-dialkylaniline) or a mixture of a 4,4'-methylene-bis-(3-chloro-2,6-dialkylaniline) with one or more aromatic or aliphatic diamines or a polyol.

9. The polyurethane system according to claim 8 wherein 4,4'-methylene-bis-(3-chloro-2,6-diethylphenylisocyanate) and, as an aromatic diamine, 4,4'-methylene-bis-(3-chloro-2,6-diethylaniline) or a mixture of 4,4'-methylene-bis-(3-chloro-2,6-diethylaniline) with one or more aromatic or aliphatic diamines or a polyol, are used.

10. The polyurethane system according to claim 7 wherein 4,4'-methylene-bis-(3-chloro-2,6-diethylphenylisocyanate) and, as an aromatic diamine, 4,4'-methylene-bis-(3-chloro-2,6-diethylphenylisocyanate) or a mixture of 4,4'-methylene-bis-(3-chloro-2,6-diethylaniline) with one or more aromatic or aliphatic diamines or a polyol, are used.

* * * * *